US007698157B2

(12) United States Patent
Ghouri

(10) Patent No.: US 7,698,157 B2
(45) Date of Patent: Apr. 13, 2010

(54) SYSTEM AND METHOD FOR MULTI-DIMENSIONAL PHYSICIAN-SPECIFIC DATA MINING FOR PHARMACEUTICAL SALES AND MARKETING

(75) Inventor: Ahmed Ghouri, San Diego, CA (US)

(73) Assignee: Anvita, Inc., San Diego, CA (US)

( * ) Notice: Subject to any disclaimer, the term of this patent is extended or adjusted under 35 U.S.C. 154(b) by 1950 days.

(21) Appl. No.: 10/456,402

(22) Filed: Jun. 6, 2003

(65) Prior Publication Data

US 2004/0049506 A1    Mar. 11, 2004

Related U.S. Application Data

(63) Continuation-in-part of application No. 10/351,083, filed on Jan. 23, 2003, now Pat. No. 7,624,029, and a continuation-in-part of application No. 10/350,483, filed on Jan. 23, 2003.

(51) Int. Cl.
*G06Q 10/00* (2006.01)
(52) U.S. Cl. .............................. 705/3; 705/2; 600/300; 600/301
(58) Field of Classification Search .................. 705/2–4
See application file for complete search history.

(56) References Cited

U.S. PATENT DOCUMENTS

| | | | |
|---|---|---|---|
| 5,833,599 A | 11/1998 | Schrier et al. | |
| 5,867,821 A | 2/1999 | Ballantyne et al. | |
| 6,024,699 A | 2/2000 | Surwit et al. | |
| 6,151,581 A | 11/2000 | Kraftson et al. | |
| 6,338,039 B1 | 1/2002 | Lonski et al. | |
| 6,421,650 B1 | 7/2002 | Goetz et al. | |
| 2002/0002474 A1* | 1/2002 | Michelson et al. | ............. 705/3 |
| 2002/0010595 A1 | 1/2002 | Kapp | |
| 2002/0019749 A1 | 2/2002 | Becker et al. | |
| 2002/0026330 A1 | 2/2002 | Klein | |
| 2002/0029223 A1 | 3/2002 | Rice et al. | |
| 2002/0032582 A1 | 3/2002 | Feeney et al. | |
| 2002/0035484 A1 | 3/2002 | McCormick | |
| 2002/0040305 A1 | 4/2002 | Nakatsuchi et al. | |
| 2002/0052760 A1 | 5/2002 | Munoz et al. | |
| 2002/0091546 A1 | 7/2002 | Christakis et al. | |
| 2002/0095313 A1 | 7/2002 | Haq | |

(Continued)

*Primary Examiner*—Vivek D Koppikar
(74) *Attorney, Agent, or Firm*—DLA Piper LLP (US)

(57) ABSTRACT

The present invention relates to a system and method for electronic and algorithmic data mining of an individual physician's prescribing history to determine the approximate distribution of diseases within their practice population for optimizing pharmaceutical sales and marketing. Rapid and large-scale determination of specific clinical safety and efficacy attributes of a marketed drug which are most pertinent and relevant to a given physician, when compared to a competitor's drug, are defined and tabularized. Major clinical characteristics taken into account include a drug's safety, efficacy, cost, dosing convenience, formulary insurance coverage, side effect profiles, and FDA approval for the intended use. A symbolic representation of knowledge is employed in which the marketed drug and each competitor's drug are compared algorithmically against each other with a scoring system that is based upon machine analysis of each major clinical characteristic. The score is further refined according to the number and severity of safety interactions which are relevant to the comparison, and also based upon predicted prevalence of such interactions within a specific physician's practice.

19 Claims, 3 Drawing Sheets

U.S. PATENT DOCUMENTS

2002/0116219 A1 8/2002 Ibok et al.
2002/0143582 A1 10/2002 Neuman et al.
2002/0147615 A1 10/2002 Doerr et al.
2002/0188466 A1 12/2002 Barrette et al.

* cited by examiner

SYSTEM AND METHOD FOR MULTI-DIMENSIONAL PHYSICIAN-SPECIFIC DATA MINING FOR PHARMACEUTICAL SALES AND MARKETING

CROSS REFERENCE TO RELATED APPLICATIONS

The present application is a continuation-in-part to U.S. patent applications Ser. Nos. 10/351,083 now U.S. Pat. No. 7,624,029 and 10/350,483, both filed Jan. 23, 2003 and entitled COMPUTERIZED SYSTEM AND METHOD FOR RAPID DATA ENTRY OF PAST MEDICAL DIAGNOSES and SYSTEM AND METHOD FOR PATIENT-SPECIFIC OPTIMIZATION OF MEDICAL THERAPY BY SIMULTANEOUS SYMBOLIC REASONING IN ALL CLINICAL DIMENSIONS, respectively. The present application is also related to copending U.S. patent applications entitled SYSTEM AND METHOD FOR CREATING AND MAINTAINING AN INTERNET-BASED, UNIVERSALLY ACCESSIBLE AND ANONYMOUS PATIENT MEDICAL HOME PAGE and SYSTEM AND METHOD FOR GENERATING PATIENT-SPECIFIC PRESCRIPTION DRUG SAFETY INSTRUCTIONS, both filed on instant date herewith. All the noted applications are commonly owned with the present application, the entire contents of all of which are expressly incorporated herein by reference.

FIELD OF THE INVENTION

The present invention relates to systems and methods for electronic medical and pharmaceutical data extraction and more particularly, for rapidly and algorithmically determining pharmaceutical safety and efficacy information which optimizes the sales and marketing of pharmaceuticals to a specific physician, subset of physicians, or other prescribing entity.

BACKGROUND OF THE INVENTION

An estimated $6 billion is spent per year by the U.S. pharmaceutical industry to provide one-on-one marketing to physicians using its sales force. The process is highly competitive, expensive, inefficient, and its attendant costs are growing rapidly. This one-to-one marketing is traditional known within the pharmaceutical industry as physician detailing. Detailing costs today are approaching $400 per physician visit, which averages 3-7 minutes of personal interaction time. Additionally, the number of sales representatives involved in drug detailing activities has grown from 35,000 to 70,000 during the preceding 6 years, yet the number of practicing physicians has remained essentially unchanged for the same period of time. The pharmaceutical industry is therefore highly concerned about rising cost trends which, if continued, are viewed as being unsustainable. Indeed, the majority of the top 20 pharmaceutical companies now spend more on sales and marketing than on research and development.

Today's marketing messages to individual physicians are generic and therefore highly inefficient. For example, representatives typically leave samples of newer medications along with published articles or clinical case reports related to safety, cost, or efficacy of the marketed drug, FDA-approved package insert information, and gifts, along with corporate brochures. Also utilized are generic marketing materials in which the marketed drug is compared against a competing drug in terms of various attributes, such as price, dosing, safety, FDA-approved indications for its use, or efficacy.

It is hoped that these aforementioned items will influence MD prescribing behavior. However, the fundamental limitation of these materials is their generic and static nature, which limits the impact they may have on the physician, and contributes to inefficient marketing. For example, generic materials do not typically (except by coincidence) explicitly address the specific needs of patients and specific economic considerations which exist within a physician's practice. For instance, a primary care physician may have 1500 hypertensive patients in his practice who are being treated with a specific high blood pressure medicine (medication "X"). A drug company may wish to market to this physician an allergy medicine (medication "A"), and consider its primary competitor allergy medicine "B". In doing so, the drug company may leave advertising materials with the physician in which the attributes of allergy drug A are contrasted to allergy drug B. However, B may not even be a relevant competitor to A, because the majority of patients in the doctors practice have insurance company formularies which do not pay for drug B in the first place. Therefore, the more relevant competitor to allergy medicine A is actually another allergy medicine "C".

Considering this particular line of reasoning, it may also be the case that allergy medicine C, the more likely competitor, has a serious drug-to-drug interaction with high blood pressure medicine X, which is used by 1500 of the physician's patients. In this scenario, a very relevant and powerful marketing message would be that allergy medicine A is safe in the doctor's patients, but allergy medicine C is dangerous. The cost effectiveness of such a message may be orders of magnitude higher than traditional generic materials which are not MD-specific.

Indeed, each physician's practice is totally unique from any other, in terms of the types and prevalence of diseases which exist, and the medications which the MD has chosen to treat those diseases. Because there are more than 500,000 practicing physicians in the U.S., manual determination of the specific and relevant elements within each physician's practice is not feasible on a vast scale. Thus, there is a need for a system which can algorithmically and rapidly determine sales and marketing safety and efficacy information which is specific to the needs of an individual physician's or physician group's patient population, and in which the marketed drug is superior to its competitors.

SUMMARY OF THE INVENTION

In a general sense, a method for optimizing pharmaceutical sales and marketing information to a specific prescribing entity comprises determining a listing of drugs typically prescribed by the prescribing entity and defining a distribution of disease among the patients of the prescribing entity's practice on the basis of drugs prescribed. A drug being marketed is scored on the basis of a safety criteria with respect to drug-drug interactions against the drugs typically prescribed by the prescribing entity and further scored on the basis of an efficacy criteria with respect to disease against the drugs typically prescribed by the prescribing entity. Drug safety and efficacy scores are adapted to be relevant to the particular disease distribution represented within the prescribing entity's practice. Superior safety and efficacy criteria of the drug being marketed with respect to the drugs typically prescribed by the prescribing entity are identified to the prescribing entity through entity/practice-specific marketing materials.

In one particular aspect of the invention, a method for optimizing pharmaceutical sales and marketing information based on a prescribing entity's prescribing history comprises obtaining a prescribing entity's prescription history for a defined time period and establishing an actual disease prevalence for the prescribing entity based on a frequency relationship between each drug prescribed by the prescribing entity and a disease for which it is prescribed. A general prevalence value is also determined for the prevalence of each disease in the general population and a weighted disease prevalence profile is established for the prescribing entity based on a combination of the general disease prevalence value and the actual practice's disease prevalence value.

A database of hierarchical medical attributes is established, the attributes being arranged in a parent-child relationship fashion in accordance with accepted medical ontology and each attribute is symbolically represented as a data object so as to facilitate electronic and algorithmic computation. The medical attributes include drug, disease and allergy term definitions, including representations of drug-drug, drug-disease and drug-condition interactions, as well as severity values for the severity of the various interactions.

In a particular feature of the invention, a severity score is generated for a particular drug-drug interaction based on a severity criteria of a drug-drug interaction dimension. A composite safety score is developed for a particular drug based on the severity score of any known drug-drug interactions and a prevalence score based on a frequency of occurrence of any known drug-disease interactions attendant to that particular drug. Selected ones of a plurality of generally related drugs are ranked on the basis of their composite safety scores and compared to a drug being marketed.

An additional feature of the present invention is the definition of relevant therapeutic endpoints for determining efficacy of a particular drug with respect to a particular indication for which it is prescribed. Advantageously, the defined therapeutic endpoints are included in the database of medical attributes. A composite efficacy score for a particular drug is determined based on its efficacy with respect to an endpoint for its associated indication and a prevalence of use score based on the prescription history of the prescribing entity. Selected ones of a plurality of generally related drugs are ranked on the basis of their composite efficacy scores and compared to the efficacy score for the particular drug being marketed.

Relevant differences in the composite safety and efficacy scores of a drug which is being marketed and particular ones of substantially similar drugs commonly prescribed by the prescribing entity are electronically and algorithmically identified and marketing material including the relevant differences is prepared for the marketed drug comparing its safety and efficacy to the particular ones of substantially similar drugs commonly prescribed by the prescribing entity. The marketing material includes safety and efficacy score comparison information for the marketed drug characterized in accordance with drug-disease interactions based on the prescribing entity's weighted disease prevalence and the prescribing entity's historical drug prescription preferences.

DESCRIPTION OF THE DRAWINGS

These and other features, aspects and advantages of the present invention will be more fully understood when considered with respect to the following specification, including associated tabular depictions, appended claims and accompanying drawings, wherein:

DESCRIPTION OF THE INVENTION

Figure 1:
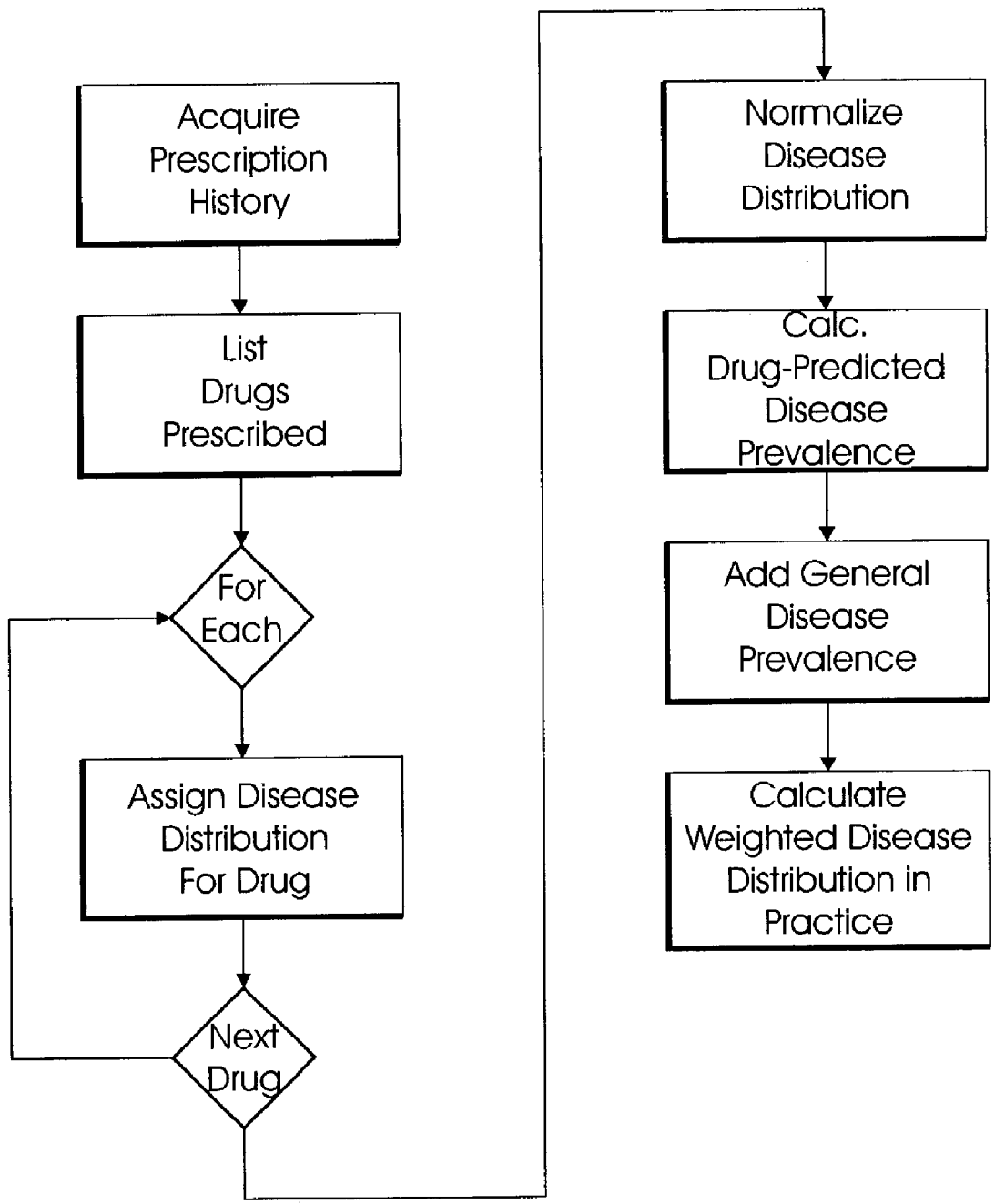
FIG. 1 is a simplified flow diagram of an exemplary determination of practice-specific disease distribution based on practice-specific drug prescription history.

The present invention relates to a system and method for electronic and algorithmic data mining of an individual physician's (or a clinically relevant subset of substantially similar physicians') prescribing history to determine the approximate distribution of diseases within their practice population in order to optimize pharmaceutical sales and marketing to that specific physician, subset group of physicians, or other prescribing entity(s). By virtue of machine-enabled symbolic reasoning, the invention enables rapid and large-scale determination of specific clinical safety and efficacy attributes of a marketed drug which are most pertinent and relevant to a given physician or physician group when compared to a competitor's drug.

In general, physicians evaluate certain attributes, which are commonly termed Major Clinical Characteristics, of a pharmacotherapy regime, when determining which medication is optimal for a patient. These major clinical characteristics include a drug's safety, efficacy, cost, dosing convenience, formulary insurance coverage, side effect profiles, and FDA approval for the intended use (e.g., for a given diagnosis, pediatric use, etc). Furthermore, within the realm of the safety attribute, there are specific sub-types of interactions which create safety risks and must, therefore be taken into consideration. These include (a) drug-drug interactions, (b) drug-disease interactions, (c) status interactions such as interactions in pregnancy, (d) interactions if breastfeeding, (e) drug-medical condition interactions, and (e) interactions in allergic states, either primary to the specific drug or cross sensitivity to a related drug for which the patient has known allergy. Examples of drug-medical condition interactions might include exacerbated responses or risks in a particular ethnic group or in patients with a particular laboratory finding which may not be considered a disease, but is clinically significant nevertheless. In the case of pregnancy, each drug is classified by the FDA as having a pregnancy risk category from A to X, and is similarly stratified for risk in breastfeeding (lactating) mothers into distinct categories.

In the present invention, a symbolic representation of knowledge is employed in which the marketed drug and each competitor's drug are compared algorithmically against each other with a scoring system that is based upon machine analysis of each Major Clinical Characteristic. The score is further refined according to the number and severity of safety interactions which are relevant to the comparison, and also based upon predicted prevalence of such interactions within a specific physician's practice.

In a particular exemplary embodiment of the invention, the sequence of events in achieving this are as follows. Initially, for each physician (or subset group of physicians) the initial step is to determine the prescription medications which are being prescribed, and the frequency in which they have been used. This kind information is routinely collected and is readily available from physician profiling companies such as IMS and Quintiles in raw, unprocessed format. Profiling information, so collected, might indicate that, for a given doctor, an exemplary prescription activity list for the preceding year might be as follows:

Drug A 279 prescriptions
Drug B 311 prescriptions
...
Drug M 5 prescriptions
Drug N 117 prescriptions Following acquisition of a physician's prescription activity, the next step of the methodology according to the invention, would involve conversion of the acquired distribution of actually used drugs into a predicted distribution of disease within that doctor's population of patients. The method by which this is determined is by reverse indexing a particular drug to the published (and unpublished but well understood) indications for which that drug is prescribable. Those having skill in the art will immediately understand that, for each drug under consideration, there is a well known set of indications for its use. For some medications, there is only one common use for that drug; an example would be azidothymidine (AZT) for which the only clinical application is the treatment of AIDS or HIV infection. Accordingly, azidothymidine (AZT) is relatively easily reverse indexed to a specific and generally unique indication.

However, for a drug like atenolol, there may be a host of possible indications that must be considered when constructing a disease distribution profile for a physician. Well known indications for Atenolol therapy include Hypertension, Migraine, Headaches, Essential Tremor, Congestive Heart Failure, Atrial Fibrillation, and the like. Notwithstanding the scope of the Atenolol possible indications list, a disease distribution may nevertheless be constructed, with respect to Atenolol, by taking under consideration the expected distribution of these major diseases within the general population. For example, it is known that certain indications have a particular prevalence within the general population, and it is assumed that Atenolol is prescribed for a particular indication at the same prevalence. Thus:

Hypertension=56% of use of atenolol
Migraine Headaches=3% of use of atenolol
Essential Tremor=1% of use of atenolol
Congestive Heart Failure=28% of use of atenolol
Atrial Fibrillation=12% of use of atenolol Given the disease distribution above, if a specific doctor wrote approximately 1000 prescriptions for atenolol within a given time period, one is able to calculate a probability distribution for approximate disease frequency within this practice, based on the generalized frequency distribution of the disease across the general population. Accordingly, such a calculated disease frequency, based on a rate of 1000 atenolol prescriptions, would be:

560 patients with hypertension;
30 patients with migraines;
10 patients with essential tremor;
80 patients with congestive heart failure; and
120 patients with atrial fibrillation.

In this manner, a reasonably accurate profile of practice's disease distribution can be constructed in accordance with the practice's frequency of Atenolol prescription. The process is repeated for each drug prescribed by the physician or physician group, and a reasonably accurate approximation of total disease distribution in the specific practice can be determined. Assigning an arbitrary designation to a predicted disease (Atrial Fibrillation=Disease 1, for example), one might arrive at an exemplary distribution as follows:

Disease 1=120 patients
Disease 2=75 patients
Disease 3=17 patients Etc. . . .

A next step in the methodology is to include common diseases based upon their overall prevalence in the general society notwithstanding a particular physician's prescribing behavior. The reason this is important is that many common diseases are not treated with prescription medications, but may be quite common nevertheless in a physician's practice due to its pervasive nature in the general population. An example of this type of common disease might include Type II diabetes, which is commonly treated by diet and exercise alone. However, because of the potential for certain drug-condition interactions that might obtain for Type II diabetes, it is important not to overlook a significant practice patient population of this disease simply because few (or no) prescriptions were written for it.

Therefore, a second registry of disease is added to the initial practice mix of diseases based on actual prescriptions. The second registry is based on expected prevalence of disease in the general population, yet normalized according to the total number of prescriptions written. In a typical internal medicine practice, for example, virtually all of the practice's patients will have been prescribed at least one medication. Therefore, the expected number of patients will approximate a constant multiplied by the total number of unique prescriptions for a given time period (i.e., in the preceding year), with the understanding that this constant will vary on a specialty-by-specialty basis. If this constant were 1.5 for example, and 2000 prescriptions were written, then one might assume that the patient population has a size of 3000 patients. The constant can be determined with fairly reasonable accuracy using historical data readily available. Now, if a Disease X in internal medicine has a prevalence of 3%, then one could predict that about 90 patients would have this condition within the doctor's practice. Thus the total disease population count in the doctor's practice might be determined as follows:

1000 prescriptions written for atenolol
=560 expected hypertensives treated with atenolol (56% of Rx is for HTN);
500 prescriptions written for furosemide (24% of Rx is for HTN);
=120 expected hypertensives treated with furosemide;
=680 total prescriptions for hypertension;
×0.50 multiplier (expected that 50% of hypertensives require more than 1 medication for hypertension)=420 patients who are treated;
×1.10 multiplier (expected that 10% of patients with hypertension do not require medical therapy at the current moment)=462 patients with hypertension in his practice.

Additionally, the prevalence of allergies can be determined based on expected overall incidences of any particular allergy in the general population, in a substantially similar fashion. For example, a generally accepted value for the of prevalence penicillin allergy in the general population is about 10%. Thus, if an exemplary practice has 3000 patients, the expected patient-incidence of penicillin allergy would represent about 300 patients.

Taking the various factors into account, it is now possible to develop a practice model summary, including disease, allergy and medication prescription distributions for any particular physician's practice. Utilizing the methodology described above, an exemplary practice might be approximated as follows:

Total Patients=4000;
Disease 1=1220 patients (calculated);
Disease 2=40 patients;
...
Disease N=840 patients;

And,
  Drug 1=1827 prescriptions (actual);
  Drug 2=43 prescriptions (actual);
  ...
  Drug N=131 prescriptions (actual);
And,
  Allergy 1=220 patients;
  Allergy 2=18 patients;
  ...
  Allergy N=22 patients.

From this distribution of medications, diseases, and allergies, one is able to determine which marketing messages can be optimally delivered to a physician in a practice-specific manner that is highly relevant to the specific physician and their practice and therefore much more likely to carry a great deal of impact.

For purposes of example, the methodology of the invention will be described in the context of a drug manufacturer who wishes to introduce and market a new antihypertensive medication, arbitrarily identified as medication A. The manufacturer may know that, in the aggregate, the major competitors for its new antihypertensive medication are existing drugs B, C, D, E, and F. However, in reality, for a given physician, drugs D and F may never (or rarely) be prescribed due to MD preference or insurance formulary coverage issues. Thus, a particularly important step in defining the scope of the actual competitive environment is to determine which of the existing drugs are the most significant actual competitors based on prescription frequency for those drugs. For each physician, or physician group, their practice model summary, including disease, allergy and medication prescription distributions is consulted and a list of competitive medications is constructed based on actual prescription frequency.

From this list, a difference table is created algorithmically in which superior attributes of the marketed drug are shown. A superior attribute can be either higher efficacy (e.g., better at lowering blood pressure for a hypertensive drug) or higher safety (fewer side effects, fewer drug-drug interactions, drug-allergy interactions, or drug-disease interactions). Superior attributes are necessarily quantifiable and reproducible.

In order for such a difference table to be created algorithmically, it is necessary to define an association between a symbolic representation of each attribute and a data object. While this definition is relatively straightforward for drugs (e.g., each drug has a unique ID for its chemical name which allows a machine to search for drug-drug interactions) this is not necessarily the case for drug-disease interactions. To understand this concept, one should consider the following exemplary scenario. Suppose a Drug A is described, according to its package insert, as contraindicated (i.e., dangerous) in patients with supra-ventricular dysrhythmias (SVD) of the heart. Additionally, Drug B, a competitor, is described, according to its package labeling, as contraindicated in patients with paroxysmal atrial tachycardia (PAT). In this exemplary scenario, if the data object associated to each drug were defined as any disease entity ID string listed in its packaging, a unique string ID for each disease entity might show up as a "difference" between the two drugs. However, for safety scoring purposes, Drug A must be assumed to be less safe than drug B, since supra-ventricular dysrhythmias are a superset of paroxysmal atrial tachycardia, and therefore encompass a broader spectrum of disease. A machine scoring system searching only for differences in ID strings for each disease term would thus be flawed, because it would not be able to extract conceptual meaning from the string ID.

The solution to the problem is the definition of a medical ontology of drugs, allergies, and diseases in which hierarchical disease term definitions are inter-related according to parent-child structure in the classical genealogical sense. In the context of creation of a drug-disease difference table for interactions, the first step is to determine for each string pair if either of the two strings is a parent of the other string. If so, then the interaction with the parent is more prevalent than the child. In general, two strings within the ontology can be either a parent-child relationship or unrelated. The difference between the two depends upon if, within the tree, a single monotonically descending pathway can be constructed in which one string is connected to the other. If so, a parent-child relationship exists.

The clinical significance of this is important. For example, a drug that is dangerous in patients with heart disease has more negative attributes associated with it than a drug which is dangerous only in patients with atrial fibrillation, a single specific type of heart disease. Thus, the safety score of the first drug would be much more favorable than that of the second drug. However, a drug with contraindication in patients with gout cannot be scored as superior to one with a contraindication in patients with anemia, as the two diseases are not conceptually related. The only scoring dimension which applies in the anemia-gout example would be related to the prevalence of each disease within the doctor's practice population. In summary, to adequately score drug-disease interactions requires prior creation of a symbolic, structured disease ontology in which appropriate comparisons can be made algorithmically in a fashion in which the results are meaningful and do not require further analysis (as would be the case in the initial PAT-SVD example above).

Figure 2:
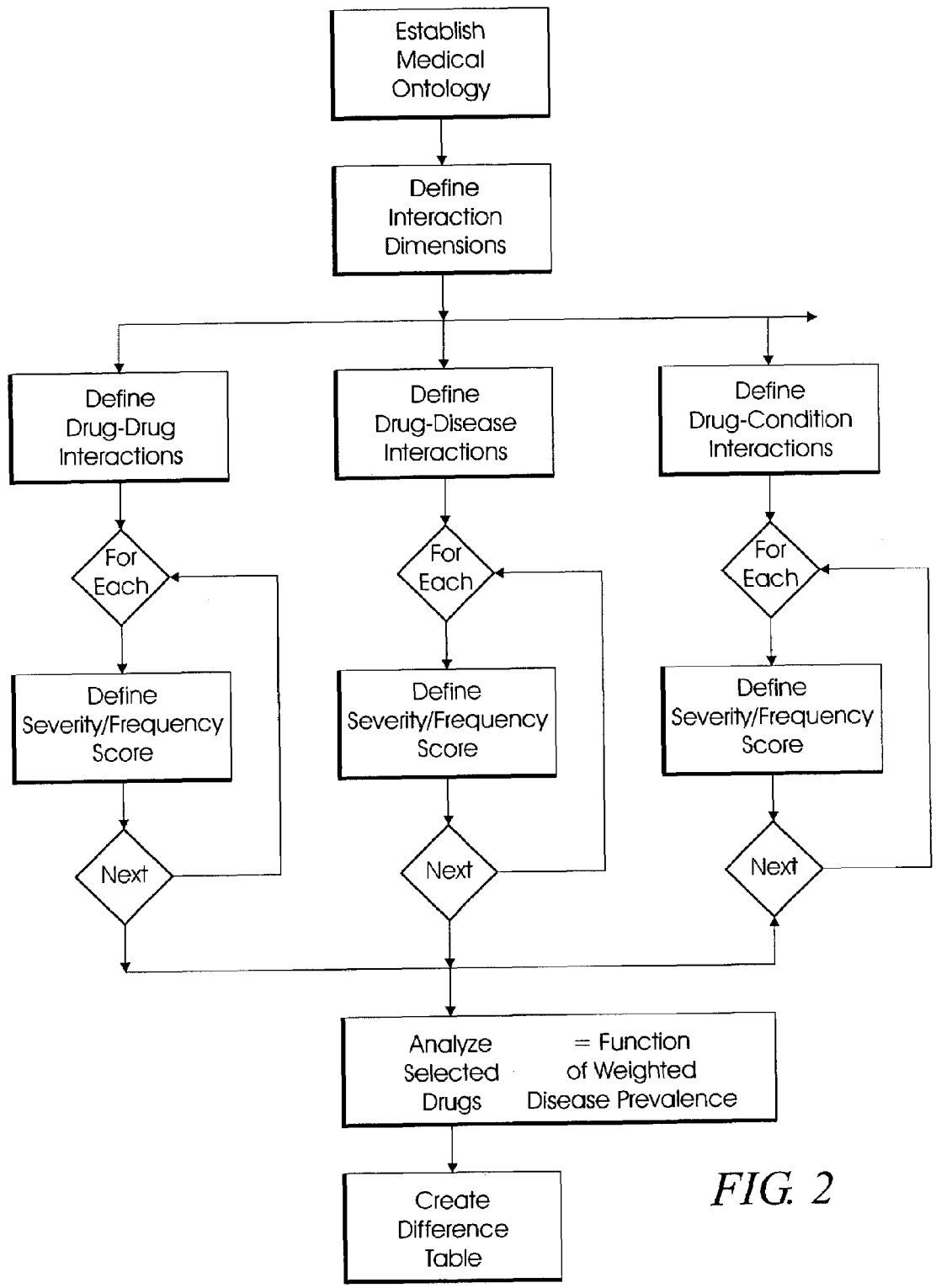
FIG. 2 is a simplified flow diagram of an exemplary determination of a safety and side-effect scoring system in accordance with the present invention.

In summary, the methodology in accordance with the present invention may be characterized as described below and with respect to the exemplary flow diagram of a method for defining safety and side-effect scoring with respect to competitive products depicted in FIG. 2. The methodology includes creation of a relevant ontology and catalog of diseases, allergies, and drugs using symbolic representations of each term to allow for machine reasoning. Such an ontology and catalog are described in copending U.S. patent applications Ser. Nos. 10/350,483 and 10/351,083, entitled SYSTEM AND METHOD FOR PATIENT-SPECIFIC OPTIMIZATION OF MEDICAL THERAPY BY SIMULTANEOUS SYMBOLIC REASONING IN ALL CLINICAL DIMENSIONS, and COMPUTERIZED SYSTEM AND METHOD FOR RAPID DATA ENTRY OF PAST MEDICAL DIAGNOSES, respectively, both commonly owned with the present application, the entire contents of which are expressly incorporated herein by reference.

Further, a predicted prevalence of disease within a doctor's specific practice population is defined. In general, two factors will determine the predicted prevalence of disease within a doctor's specific practice population, the prevalence of specific diseases within the general society (including corrections for proportions of those diseases which are not treated), and prevalence of particular diseases interpolated from a physician's prescribing habits, which may reflect the doctor's interest in treating specific diseases (e.g., he/she may be a referral specialist for a rare disease).

A Drug-Predicted Prevalence (distribution) of diseases within the practice is constructed based upon actually known medications prescribed by a physician (or subset of physicians), obtained from historical data, and the known uses of those drugs. This model is easily modified using coefficient multipliers, for example, to account for the use of multiple drugs to treat a single disease. Certainly, such coefficient multipliers may be enhanced over time with experience and with evolving uses for particular drugs. The foregoing allows one to establish a prediction of the Weighted Prevalence of Disease (both treated and untreated) in the doctor's practice. This predicted prevalence of each disease is then scored according to the percentage of patients expected to have the disease. A similarly constructed distribution of allergies, based upon the expectation of an allergy within general population data, is combined with actual prescription data using similarly obtained appropriate coefficient multipliers.

For each competitive product, all drug-drug, drug-disease, and drug-allergy adverse interactions, which do not exist for the marketed drug, are delineated in tabular form (i.e., a difference table is created allowing for managed comparisons). Further, for each delineated interaction, a Composite Safety Score is determined, with the composite based upon a severity score (mild, moderate, life threatening, for example) of the interaction combined with an expected prevalence score (rare, occasional, frequent, for example) for both the disease (in the case of a drug-disease interaction) or the frequency of actual drug use (in the case of a drug-drug interaction). The Composite Safety Score is sorted from most relevant to least relevant (highest to lowest) and the particular drug being marketed may now be repeatably and quantifiably compared with competitive products in a manner that is relevant to a particular physician and their practice.

Figure 3:
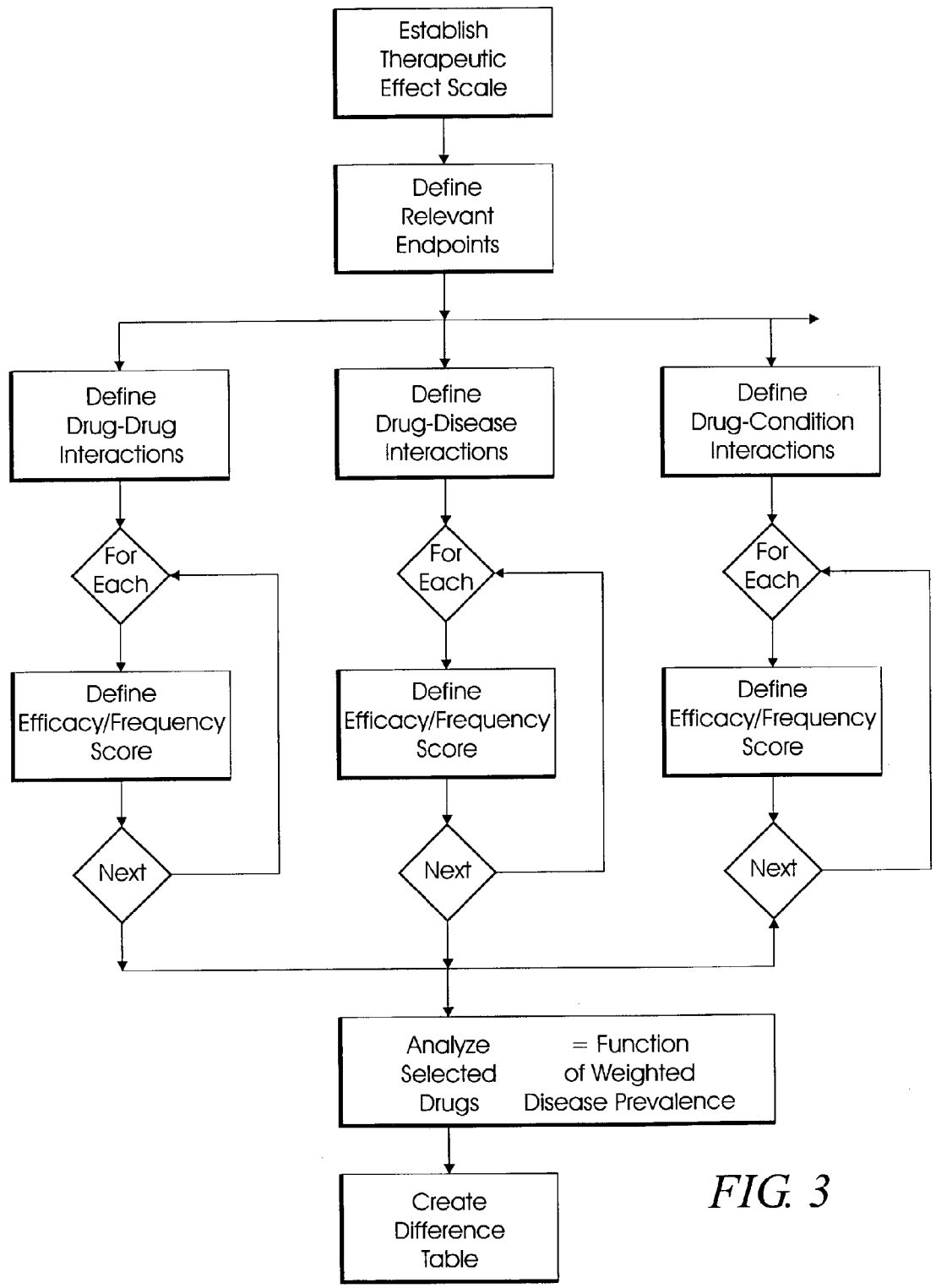
FIG. 3 is a simplified flow diagram of an exemplary determination of an efficacy scoring system in accordance with the present invention.

In a substantially similar fashion, the methodology in accordance with the present invention is particularly suitable for determination of an efficacy score for a marketed drug with respect to its competitors, as depicted in the exemplary flow diagram of FIG. 3. In the exemplary embodiment of FIG. 3, for each drug and specific indication (e.g., atenolol for hypertension), suitable therapeutic endpoints, based on FDA-approved marketing literature, are determined for the drug being marketed with respect to its competitor(s).

A Composite Efficacy Score is created for each drug in terms of efficacy toward that determined endpoint (e.g., lowering of cholesterol in mg/dL) combined with the prevalence for the use of a competitor's drug in which efficacy scores are different. It will be understood that numerical scores are able to be normalized into broad categories, such as no difference, mild difference, moderate difference, and large difference, for ease of use in data mining.

The Composite Efficacy Score for the aggregate of drugs is then sorted in accordance with a hierarchical difference rating and the particular drug being marketed may now be repeatably and quantifiably compared with competitive products in a manner that is relevant to a particular physician and their practice.

A specific example of the use of this methodology, in a hypothetical scenario to determine a Composite Safety Score is described below. In the example, data acquired on an arbitrary Doctor John Smith indicates that Dr. Smith has written 4000 prescriptions in the preceding one year period. Dr. Smith's prescription activity is known by both the particular drug name and the number written for each drug. The Drug-Predicted Prevalence of disease in his practice may now be determined, based on this information. As described above, all possible uses of each drug are determined (by indications), along with the distribution of these uses in accord with historical information. As discussed in the atenolol example above, it is known what percentage of atenolol is prescribed for heart failure, what percentage is prescribed for high blood pressure, and the like. For each given disease (indication), a Weighted Prevalence of Disease is determined, which is a weighted average of the General Disease Prevalence in the population at large, combined with the disease frequency based on actual prescribing history. Such a Weighted Prevalence of Disease can be constructed as follows:

| General Disease Prevalence | Drug-Predicted Prevalence | Weighted Prevalence (Z) |
|---|---|---|
| Disease 1 = A% | Disease 1 = B% | = ci di ei A + cj dj ejB |
| Disease 2 = C% | Disease 2 = D% | = ci di ei C + cj dj ejD |
| Disease N, etc. | Disease N, etc. | etc . . . |

In the above example, coefficients (ci and cj) are numbers which reflect the weighting of the likelihood of disease prevalence in society versus that of the drug-predicted prevalence. Coefficients di and dj are additional coefficients which serve to adjust for the proportion of patients which are expected to have the disease but need not be treated with medications. Coefficients ei and ej reflect the proportion of patients with a disease which are treated with more than one medication (to adjust for double-counting of disease). From this construction above, one is able to generate the Weighted Disease Prevalence (Z) in Dr. Smith's practice given only the known drug prescription count from historical information on the doctor.

A further step in this tabulation is obtaining the frequency of allergies, which in general will not be obtainable or predictable in a doctor-specific fashion, but can be assumed to be distributed evenly across the general population. It should be noted that in the example which follows, allergies are the clinically relevant metric chosen for analysis. However, it will be understood by those having skill in the medical arts, that any of the various other clinically relevant interaction dimensions, such as drug-condition, drug-pregnancy, and drug-lactation, can be analyzed in the context of the invention and provide a basis for suitability scoring and comparison. The allergy dimension is used here for purposes of example and simplicity of presentation only. The final tabulation for Dr. Smith's exemplary practice might look as follows:

| WEIGHTED DISEASE PREV. | DRUGS IN USE BY MD | ALLERGIES |
|---|---|---|
| Disease 1 = $Z_1$% | Drug 1 = $A_1$% | Substance 1 = $B_1$% |
| Disease 2 = $Z_2$% | Drug 2 = $A_2$% | Substance 2 = $B_2$% |
| Disease 3 = $Z_3$% | Drug 3 = $A_3$% | Substance 3 = $B_3$% |
| etc | etc | etc |

From the above data set, one may now determine a Composite Safety Score and a Composite Efficacy Score in accord with the invention. As a reminder, the Weighted Disease Prevalence value is a calculated parameter, Drugs in Use by MD is a known historical list with known associated frequencies of each entry, and the distribution of Allergies is taken from the population at large and is known from national statistical reporting.

Using the methodology of the present invention, it is now possible to algorithmically compare a hypothetical Drug A against its competitors B and C, given the above defined parameters. The first thing which is done is to search for all possible drug-drug, drug-disease, and drug-allergy interactions which exist for A, B, and C and, once obtained, rank the interactions (score them) on the basis of severity. Next, remove all interactions which exist in Drugs B and C which identically exist for Drug A (it is desired to show how A is superior to B, and C). In this example, drugs with a numerical designation are those prescribed by the doctor in his practice and do not include A, B, or C. For each type of interaction, a Safety Score is defined as a composite number which reflects the severity of the interaction (hence its clinical relevance) and the expected frequency of the interaction. For example, a less frequent interaction which is life threatening may be of higher clinical importance that a frequent interaction which is mildly undesirable and tolerable by the patient.

In general, one is able to define the composite product of frequency-times-severity as a Safety Score, in which the elements of frequency and safety are not required to be strictly linear, so long as they are ordered. For instance, severity of interaction can range along a spectrum from 1=minimal, 3=moderate, 25=severe, and 100=life threatening. In this case, life threatening is weighted quite highly due to its clinical significance. Similarly, frequency can be categorized into broad clinical classifications, such as 1=prescribed in less than 1% of patients, 3=prescribed in 2-10% of patients, 10=prescribed in 11-33% of patients, 50=prescribed 34-50% of patients, and 100=prescribed in >50% of patients. As should be fully understood, the definition of natural clinical categories and the corresponding weighting values described above are determined empirically and refined over time. The specific numerical values given in the preceding exemplary embodiment are purely arbitrary and given solely for purposes of descriptive ease. The present invention does not depend on any given numerical value, but rather that a value (whether numerical or otherwise ordered) is assignable so as to provide for algorithmic computation.

In the general sense, scoring will depend upon both a product score (frequency×severity) and a weighted summation score, with the scores typically added together. The weighted summation score can be generalized as $C_i$×frequency+$C_j$×severity. Therefore, the final score is generally frequency×severity+$C_i$×frequency+$C_j$×severity. For simplicity purposes, the weighted summation score element is not used below (coefficients $C_i$ and $C_j$ are taken as zero for illustrative clarity). An exemplary table of drug-drug interactions found in two competitive medications (competitive drugs B and C) that are not found in the particular drug being marketed (i.e., drug A) is shown below.

| Interacting Drug | Severity Score | Frequency Score | Safety Score |
|---|---|---|---|
| Drug B Interactions: | | | |
| Drug 13 | 100 | 50 | 5000 |
| Drug 217 | 25 | 50 | 1250 |
| Drug 124 | 25 | 10 | 250 |
| Drug 12 | 25 | 3 | 75 |
| Drug C Interactions: | | | |
| Drug 13 | 100 | 50 | 5000 |
| Drug 217 | 25 | 10 | 250 |
| Drug 38 | 3 | 10 | 30 |

From this exemplary interaction table, one is able to rapidly conclude that a focused, practice-specific, and relevant marketing message to this particular doctor (Dr. Smith) would be that Drug A is substantially safer in all of his patients who are concurrently taking Drugs 13 and 217, than competitive products B and C. This fact can have extreme significance in a physician's practice because many patients today are elderly and take numerous medicines perpetually because the underlying disease is incurable (e.g., Parkinson's disease, diabetes, high blood pressure). In this example, Drugs 13 and 217 might well represent chronic medications that are prescribed by the doctor for more than a third of his patients.

Were drugs A, B, and C competitors for the treatment of a common problem, such as mild to moderate pain, which a very high proportion of his patients on chronic medications may undoubtedly request at some point (e.g., following a sprain), a very effective marketing message would therefore be that drug A is safer than competitive drug B or C in patients who are also taking drug 13 or drug 217. Extrapolating the methodology to yet additional clinical interaction dimensions, if the above table were for drug-disease interactions, one would be able to determine that drug A is safer than B or C in patients with diseases 13 and 217, which may be commonly treated in his practice.

The present invention therefore represents a substantial improvement over the inefficient and generic marketing messages which are found in physicians' journals today. Because the present invention is algorithmic and utilizes symbolic reasoning, one is able (given a list of historical medications prescribed by the MD) to determine optimal safety and efficacy messages to be delivered to the MD at issue, in an automated and practice-specific fashion. Consequently, a computer-based system which employs the present invention could provide this valuable and compelling information rapidly, and on a massive scale (e.g., there are nearly 600,000 practicing in the U.S. alone).

It should be noted that the Composite Efficacy Score utilizes the same methodology as that for Safety, excepting terminology; only the semantics are different. For example, in safety scoring, interactions are negative in nature (adverse, undesired effects) whereas in the case of efficacy one is looking for positive (desirable and therapeutic) effects. For example, the drug-disease interaction for cisapride with respect to prolonged QT syndrome is severe and life threatening. The Composite Safety Score for this interaction may be highly significant as the score is a function of the weighted prevalence of prolonged QT syndrome in the doctor's practice as well as by a function of the severity of the interaction (e.g., a severity of 10=life threatening, while a severity of 1=mild).

On the other hand, the 'interaction' between atenolol and high blood pressure (for which it is prescribed) might be quantified as the proportion of patients who achieve control of their high blood pressure on this medication after 1 month of use. The endpoints by which efficacy scores are determined will in general be based upon the endpoints used in clinical studies. For purposes of clarity, the present invention distinguishes between desired interactions as 'efficacy' and undesirable interactions as 'safety', although the methodology is the same.

To further illustrate this point, even desirable drug-drug interactions can be quantified into an efficacy score. For instance, drug A may achieve better therapeutic results in patients who are, coincidentally, also taking a commonly prescribed medication B for another disease. This is highly significant because drug B may be the drug of choice for a common disease and cannot be substituted. In this scenario, drug A, for treatment of its intended disease, may be superior to its competitors when administered in patients already taking drug B, even though both are designed for the treatment of unrelated diseases.

In summary, the above described methodology considers all important clinical interaction dimensions using a symbolic representation of disease entities combined with statistical appreciation of disease prevalence in the general population as well as an actual disease prevalence in a particular practice calculated on the basis of a practice's prescription history and the statistical distribution of indications for which a particular drug is described. The invention allows for automated inferencing by machine which can present drug therapy choices that are ranked or scored, in a practice-specific fashion, for interaction safety and therapeutic efficacy. Ranking and scoring is performed as a comparison between a specific drug which is being marketed and its most relevant competitors, particularly with respect to safety and efficacy in the specific patient distribution represented in the practice.

Accordingly, the present invention can be understood as defining a particular system and methodology by which pharmaceutical sales and marketing activities can be organized in a physician and practice-specific fashion and in which critical and clinically relevant information is delivered to the physician without substantial and individualized research and analysis by a pharmaceutical manufacturer. While the above specification has shown, described and identified several novel features of the invention, as applied to various exemplary and illustrated embodiments, it will be understood that the embodiments are for purposes of illustration and ease of description only. Various omissions, substitutions and changes in the form and details of the exemplary embodiments may be made by those skilled in the art without departing from the scope and spirit of the present invention. Accordingly, the invention is not contemplated as being limited to the described, exemplary and illustrated embodiments, but are rather defined by the scope of the appended claims.

The invention claimed is:

1. A method for optimizing pharmaceutical sales and marketing information based on a prescribing entity's prescribing history on a computer-based system, the method comprising: obtaining a prescribing entity's prescription history for a defined time period; establishing an actual disease prevalence for the prescribing entity based on a frequency relationship between each drug prescribed by the prescribing entity and a disease for which it is prescribed; determining a general prevalence value for each disease in the general population; and establishing, by a computer, a weighted disease prevalence profile for the prescribing entity based on a mathematical combination of an adjusted general prevalence value and an adjusted actual prevalence value, wherein the adjusted general prevalence value and the adjusted actual prevalence value are adjusted based on the proportion of patients who have untreated disease and diseases requiring at least one drug.

2. The method according to claim 1, further comprising: establishing a database of hierarchical medical attributes, the attributes arranged in a parent-child relationship fashion in accordance with medical ontology; and symbolically representing each attribute as a data object.

3. The method according to claim 2, wherein the medical attributes include drug, disease and allergy term definitions, the method further comprising: establishing interaction dimensions between and among the drug, disease and allergy term definitions; and defining a severity score for a particular drug based on the severity of a drug-drug interaction dimension.

4. The method according to claim 3, further comprising: determining a composite safety score for a particular drug based on the severity score of the drug-drug interaction and a prevalence score based on a frequency of occurrence of a drug-disease interaction; and ranking selected ones of a plurality of generally related drugs on the basis of their composite safety scores.

5. The method according to claim 4, further comprising: determining relevant therapeutic endpoints for determining efficacy of a particular drug with respect to a particular indication for which it is prescribed, the endpoints included in the database of medical attributes; determining a composite efficacy score for a particular drug based on its efficacy with respect to an endpoint for its associated indication and a prevalence of use score based on the prescription history of the prescribing entity; and ranking selected ones of a plurality of generally related drugs on the basis of their composite efficacy scores.

6. The method according to claim 5, further comprising: identifying differences in the composite safety and efficacy scores of a drug which is being marketed and particular ones of substantially similar drugs commonly prescribed by the prescribing entity; and preparing marketing material for the marketed drug comparing its safety and efficacy to the particular ones of substantially similar drugs commonly prescribed by the prescribing entity.

7. The method according to claim 6, wherein the marketing material includes safety and efficacy score comparison information for the marketed drug characterized in accordance with drug-disease interactions based on the prescribing entity's weighted disease prevalence.

8. A method for optimizing pharmaceutical sales and marketing information to a specific prescribing entity on a computer-based system, the method comprising: acquiring a prescribing entity's prescription history including a listing of prescribed drugs and a frequency of prescription of each drug; determining a disease distribution among the individuals comprising the prescribing entity's practice on the basis of the prescription history; establishing, by a computer, a drug safety score on the basis of a severity criteria and a frequency criteria for at least known drug-drug and drug-disease interactions between and among a plurality of substantially similar drugs; and ranking the plurality of substantially similar drugs on the basis of the drug safety score and a prevalence criteria determined by the prevalence of use of a particular drug by the prescribing entity and the prevalence of occurrence of a particular disease within the prescribing entity's practice wherein the prevalence criteria is adjusted based on the proportion of patients who have untreated disease and diseases requiring at least one drug.

9. The method according to claim 8, further comprising: establishing a drug efficacy score on the basis of a drug's efficacy towards a defined therapeutic endpoint for each of the plurality of substantially similar drugs; and ranking the plurality of substantially similar drugs on the basis of the drug efficacy score and a prevalence criteria determined by the prevalence of use of a particular drug within the prescribing entity's practice.

10. The method according to claim 9, further comprising: comparing the safety and efficacy score of a drug being marketed against the safety and efficacy scores of the plurality; identifying particular ones of the drugs commonly prescribed by the prescribing entity that exhibit lower safety and/or efficacy scores from the drug being marketed; and identifying those drug-drug and/or drug-disease interactions for which the drug being marketed exhibits superior scores than the drugs commonly prescribed by the prescribing entity.

11. The method according to claim 10, further comprising: establishing a database of hierarchical medical attributes, the attributes arranged in a parent-child relationship fashion in accordance with medical ontology; and symbolically representing each attribute as a data object.

12. The method according to claim 11, wherein the medical attributes include drug-drug interaction, drug-disease and allergy term definitions, the method further comprising: establishing a severity and a frequency of occurrence criteria between and among the term definitions; and defining the severity score for a particular drug based on the severity of a drug-drug interaction criteria.

13. The method according to claim 12, further comprising: determining a composite safety score for a particular drug based on the severity score of the drug-drug interaction and a prevalence score based on a frequency of occurrence of a drug-disease interaction; and ranking the a plurality of generally related drugs on the basis of their composite safety scores.

14. A method for optimizing pharmaceutical sales and marketing information to a specific prescribing entity on a computer-based system, the method comprising: determining a listing of drugs prescribed by the prescribing entity; defining, by a computer a distribution of disease among the patients of the prescribing entity's practice on the basis of drugs prescribed to generate a weighted disease prevalence that is adjusted based on the proportion of patients who have untreated disease and diseases requiring at least one drug; scoring a drug being marketed on the basis of a safety criteria with respect to drug-drug interactions against the drugs prescribed by the prescribing entity; scoring a drug being marketed on the basis of an efficacy criteria with respect to disease against the drugs prescribed by the prescribing entity; and identifying safety and efficacy criteria of the drug being marketed with respect to the drugs prescribed by the prescribing entity.

15. The method according to claim 14, further comprising: establishing an actual disease prevalence for the prescribing entity based on a frequency relationship between each drug prescribed by the prescribing entity and a disease for which it is prescribed; determining a general prevalence value for each disease in the general population; and establishing a weighted disease prevalence profile for the prescribing entity based on a combination of the general prevalence value and the actual prevalence value.

16. The method according to claim 15, further comprising: establishing a database of hierarchical safety and efficacy attributes, the attributes arranged in a parent-child relationship fashion in accordance with medical ontology; and symbolically representing each attribute as a data object.

17. The method according to claim 16, wherein the attributes include drug, disease and allergy term definitions, the method further comprising: establishing interaction dimensions between and among the term definitions; and defining an interaction severity score for a particular drug based on the severity of a drug-drug interaction dimension.

18. The method according to claim 17, further comprising: determining a composite safety score for a particular drug based on the severity score of the drug-drug interaction and a prevalence score based on a frequency of occurrence of a drug-disease interaction; and ranking selected ones of a plurality of generally related drugs on the basis of their composite safety scores.

19. The method according to claim 18, wherein the determining and ranking steps are performed by computational operation on the data objects, such that the identification of superior safety and efficacy criteria of the drug being marketed with respect to the drugs prescribed by the prescribing entity is performed electronically.

* * * * *